United States Patent [19]

Darke et al.

[11] Patent Number: 5,891,661
[45] Date of Patent: Apr. 6, 1999

[54] LOW TEMPERATURE ASSAY FOR ACTIVE HCMV PROTEASE IN DIMERIC FORM

[75] Inventors: Paul L. Darke, Blue Bell; Lawrence C. Kuo, Gywnedd, both of Pa.

[73] Assignee: Merck & Co., Inc., Rahway, N.J.

[21] Appl. No.: 823,932

[22] Filed: Mar. 25, 1997

Related U.S. Application Data

[60] Provisional application No. 60/014,108 Mar. 26, 1996.
[51] Int. Cl.$^6$ .............................. C12Q 1/37; C12N 9/50
[52] U.S. Cl. ............................................. 435/23; 435/219
[58] Field of Search ....................................... 435/23, 219

[56] References Cited

U.S. PATENT DOCUMENTS

| | | | |
|---|---|---|---|
| 5,434,074 | 7/1995 | Gibson et al. | 435/219 |
| 5,506,115 | 4/1996 | Toth et al. | 435/23 |
| 5,618,685 | 4/1997 | Darke et al. | 435/23 |

OTHER PUBLICATIONS

Y–Z Shu et al, *J. Nat Prod*, 60, pp. 529–532 (1997).
N A Abood et al., *Bioorganic & Medicinal Chem Ltrs*, 4(16); pp. 2105–2108 (1997).
W. Ogilvie, et al., *J. Med Chem.*, 40; pp. 4113–4135 (1997).
Baum et al. (1996) Biochemistry, 35(18), "Flavins Inhibit Human Cytomegalovirus UL80 Protease via Disulfide Bond Formation", pp. 5847–5855.
LaFemina et al. (1996) J. Virol., 70(7), "Characterization of a Soluble Stable Human Cytomegalovirus Protease and Inhibition By M–site Peptide Mimics", pp. 4819–4824.
Holskin et al. (1995) Anal. Biochem., 227(1), "A Continuous Fluorescence–based Assay of Human Cytomegalovirus Protease Using a Peptide Substrate", pp. 148–155.
Welch et al. (1991) Proc. Natl. Acad. Sci., USA, 88 (23). "A Herpervirus Maturational Proteinase Identification of its Gene Putative Active Site Domain and Cleavage", pp. 10792–10796.
Deckman et al. (1992) J. Virol, 66 (12), "Herpes Simplex Virus Type 1 Protease Expressed in *Escherichia–coli* Exhibits Autoprocessing and Specific Cleavage of the ICP35 Assembly Protein", pp. 7362–7367.
Baum et al. (1993) J. Virol., 67 (1) "Expression and Analysis of the Human Cytomegalovirus UL80–Encoded Protease: Identification of Autoproteolytic Sites", pp. 497–506.
Dilanni et al. (1993a) J. Biol. Chem., 268 (3), "Identification of the Herpes Simplex Virus–1 Protease Cleavage Sites by Direct Sequence Analysis of Autoproteolytic Cleavage Products", pp. 2048–2051.
Dilanni et al. (1993b) J. Biol. Chem., 268 (34) "In Vitro Activity of Herpes Simplex Virus Type 1 Protease with Peptide Substrates", pp. 25449–25454.
Smith et al. (1994) Methods Enzymol., 244 (Proteolytic Enzymes: Serine and Cysteine Peptidases), "Purification and Kinetic Characterization of Human Cytomegalovirus Assemblin", pp. 412–423.
Burck et al. (1994) J. Virol., 68 (5), "Human Cytomegalovirus Maturational Proteinase: Expression in *Escherichia coli*, Purification and Enzymatic Characterization by Using Peptide Substrate Mimics of Natural Cleavage Sites", pp. 2937–2946.
Darke et al. (1995) J. Biol. Chem., 269 (29), "Purification of Active Herpes Simplex Virus–1 Protease Expressed in *Escherichia coli*", pp. 18708–18711.
Yamanaka et al. (1995) J. Biol. Chem., 270 (50), "Stimulation of the Herpes Simplex Virus Type 1 Protease by Antichaeotrophic Salts", pp. 30168–30172.
Pinko, et al., *J. Biol. Chem.*, 270, p. 23634 (1995).
La Femina, E.L. et al., *J. Gen. Vir.*, 64; p. 373 (1983).
Chee, M.S., et al., *Curr. Top Microbiol. Immunol.*, 154; p. 125 (1990).
Sardana, V., et al. *J. Biol. Chem.*, 269, p. 143339 (1994).
Smith, J.A,. et al., *J. Virol.*, 69(3); pp. 1734–1740,( 1995).
Messerle, M., et al., *Virus Genes*, 10(1), pp. 73–80 (1995).
Nicholas, J., *Virol.*, 204; pp. 738–750 (1994).

*Primary Examiner*—Jon P. Weber
*Attorney, Agent, or Firm*—Sylvia A. Ayler; Mark R. Daniel; LaVonda R. De Witt

[57] ABSTRACT

At low temperature, the protease of human cytomegalovirus (HCMV) is rendered highly active as a dimer of identical units. The protease is useful as a screening tool for HCMV antivirals as well as a diagnostic tool for diseases resulting from HCMV infection.

3 Claims, 2 Drawing Sheets

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

GCTAGGCTCA TATGACGATG GACGAGCAGC AG    32

( 2 ) INFORMATION FOR SEQ ID NO:2:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GCTAGGCTAG ATCTTTACGC CTTGACGTAT GACTCGC    37

( 2 ) INFORMATION FOR SEQ ID NO:3:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: protein ( v ) FRAGMENT TYPE: N-terminal ( x i ) SEQUENCE DESCRIPTION: SEQ ID NO:3:

Gly Val Val Asn Ala Ser Cys Arg Leu Arg Arg
1                  5                          10

( 2 ) INFORMATION FOR SEQ ID NO:4:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: protein ( v ) FRAGMENT TYPE: N-terminal ( x i ) SEQUENCE DESCRIPTION: SEQ ID NO:4:

Arg Gly Val Val Asn Ala Ser Ser Arg Leu Ala
1                  5                          10

( 2 ) INFORMATION FOR SEQ ID NO:5:

( i ) SEQUENCE CHARACTERISTICS:
        ( A ) LENGTH: 8 amino acids
        ( B ) TYPE: amino acid
        ( C ) STRANDEDNESS: unknown
        ( D ) TOPOLOGY: unknown ( i i ) MOLECULE TYPE: protein ( v ) FRAGMENT TYPE: N-terminal ( x i ) SEQUENCE DESCRIPTION: SEQ ID NO:5:

Arg Trp Gly Val Val Asn Ala Ser
1               5

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: protein ( v ) FRAGMENT TYPE: N-terminal ( x i ) SEQUENCE DESCRIPTION: SEQ ID NO:6:

Arg Leu Ala Thr Arg
1               5

LOW TEMPERATURE ASSAY FOR ACTIVE HCMV PROTEASE IN DIMERIC FORM

This application claims Benefit of Provisional Application Ser. No. 60/014,108, filed Mar. 26, 1996.

BACKGROUND OF THE INVENTION

This application is related to Merck Case 19262, U.S. Ser. No. 08/323,953, filed Oct. 17, 1994.

The human cytomegalovirus (HCMV) is the etiological agent of a variety of infectious diseases in infants and children. The virus also is involved in severe infections of adults with immunodeficiencies, such as AIDS patients or transplant recipients. The HCMV encodes a protease that participates in the maturation of the viral capsid. The enzyme processes the viral assembly protein within the capsid core by mediating cleavage between the ala-ser peptide bond at residue positions 308/309. This results in the linked extrusion of the assembly protein and the encapsidation of the viral genomic DNA.

The association of the individual assembly proteins into the capsid likely results from specific intermolecular protein interactions. The presence of the protease at the N-terminus of a 80 kD precursor that also contains the assembly protein assures localization of the enzyme in the capsid as a consequence of interactions mediated by the assembly protein portion. A mutant of the herpes simplex virus type 1 (HSV-1), which expresses temperature-sensitive alterations in the protease, is incapable of processing the assembly protein and encapsidating genomic DNA at the non-permissive temperature. This result indicates that a specific potent inhibitor of the viral enzyme would be useful as a therapeutic agent.

Applicants have discovered that a highly active form of HCMV protease is a dimer of identical units. At ambient or higher temperatures, most of the protease dissociates into its monomeric form which is inactive as gauged by kinetic assays. For this reason, the activity of this protease has been erroneously believed to be very low. Having an equilibrium of monomer and dimer of an enzyme in solution with the inactive monomer at high concentration will obscure detection of inhibitors of the active, dimeric form of the enzyme. This physiochemical phenomenon is governed by thermodynamic principles. Due to the high activation energy required for dissociation, the HCMV protease can be "frozen" in its active, dimeric form at about 0° C., thus enabling sensitive detection of inhibitors of this enzyme. The assay of this present invention provides a screening protocol, conveniently carried out at 0° C., for inhibitors of the HCMV protease. The existence of the HCMV protease has been reported, e.g., see Pinko, et al., J. Biol. Chem. 270, 23634 (1995). Assays for the catalytic activity of this enzyme have been described, albeit the reported kinetic parameters were substantially lower than those measured by applicants. Since the dissociation of the dimeric HCMV protease into its inactive monomeric form is responsible for the apparent low activity of the enzyme, the enzyme is "frozen" in its dimeric form by lowering the temperature of the assay and related operations to about 0° C. This approach affords an assay for the activity of the protease at low concentration ($\leq 20$ nM), thus permitting detection of weak inhibitors or strong inhibitors at low concentration.

The resulting highly active assay for HCMV protease is useful as a screening tool for HCMV antivirals in the potency range of about 100–200 nM (or less), as well as a diagnostic tool for diseases resulting from HCMV infection.

SUMMARY OF THE INVENTION

A newly discovered protocol in the assay for HCMV protease inhibition allows for highly sensitive measurement of inhibition. The assay is useful as a screening tool for HCMV antivirals, as well as a diagnostic tool for diseases resulting from HCMV infection.

DETAILED DESCRIPTION OF THE INVENTION

Figure 1:
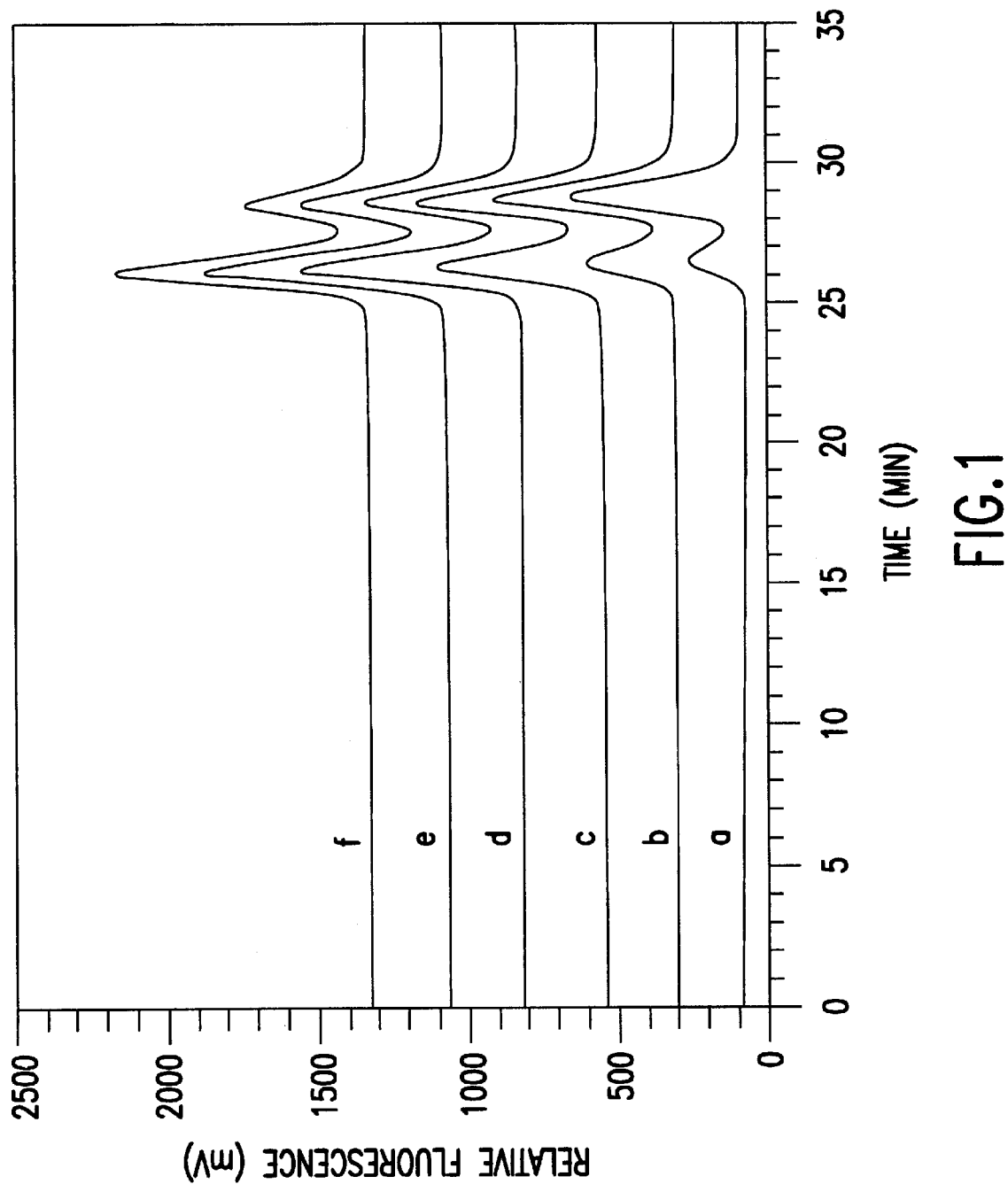
FIG. 1. Size exclusion chromatography of the HCMV protease. Samples of HCMV protease in 20% glycerol were maintained at 30° C. for at least 90 min. prior to chromatography at 10° C. Elution profiles for samples at concentrations, prior to injection, of 171 nM (a), 355 nM (b) 891 nM (c), 1975 nM (d), 2977 nM (e) and 4501 nM (f). Shown here are the protease fluorescence emission data at 350 nm. Injection volumes were adjusted to give the same total protein injected (30 pmol, monomer equivalents).

The present invention encompasses a low temperature assay for the detection of compounds that inhibit HCMV protease, said assay having a procedure comprising the steps of:

(a) providing a quantity of a compound or compounds to be assayed;

(b) incubating said compound or compounds with HCMV protease at a temperature between about 10° C. and about −10° C. in a substrate cleavage assay; and (c) determining the inhibition of said protease.

The assay is preferably carried out at a temperature range of between about 2° C. and about −2° C.

The assay is also preferably carried out at a temperature of about 0° C.

The present invention also encompasses a compound that inhibits HCMV protease with $IC_{50} \leq 200$ nM, as measured by the low temperature assay of the present invention.

One utility for the low temperature assay of the present invention is a screening assay for the detection of compounds that inhibit HCMV protease. This assay has a procedure comprising the steps of:

(a) providing a quantity of a compound or compounds to be assayed;

(b) incubating said compound or compounds with HCMV protease at a temperature between about 10° C. and about −10° C. in a substrate cleavage assay; and (c) determining the inhibition of said protease.

Expression of HCMV Protease in a Recombinant Expression System

It is now a relatively straightforward technology to prepare cells expressing a foreign gene. Such cells act as hosts and include E. Coli, B. subtilis, yeasts, fungi, plant cells or animal cells. Expression vectors for many of these host cells have been isolated and characterized, and are used as starting materials in the construction, through conventional recombinant DNA techniques, of vectors having a foreign DNA insert of interest. Any DNA is foreign if it does not naturally derive from the host cells used to express the DNA insert. The foreign DNA insert may be expressed on extrachromosomal plasmids or after integration in whole or in part in the host cell chromosome(s), or may actually exist in the host cell as a combination of more than one molecular form. The choice of host cell and expression vector for the expression of a desired foreign DNA largely depends on availability of the host cell and how fastidious it is, whether the host cell will support the replication of the expression vector, and other factors readily appreciated by those of ordinary skill in the art.

The technology for recombinant procaryotic expression systems is now old and conventional. The typical host cell is E. Coli. The technology is illustrated by treatises such as Wu, R (ed) Meth. Enzymol., 68 (1979) and Maniatis, T. et al., Molecular Cloning: A Laboratory Manual Cold Spring Harbor 1982.

The foreign DNA insert of interest comprises any DNA sequence coding for HCMV (or stable mutant thereof) of the present invention, including any synthetic sequence with this coding capacity or any such cloned sequence or combination thereof. For example, HCMV peptides coded and expressed by an entirely recombinant DNA sequence is encompassed by this invention.

Vectors useful for constructing eukaryotic expression systems for the production of recombinant HCMV comprise the DNA sequence for HCMV or variant thereof, operatively linked thereto with appropriate transcriptional activation DNA sequences, such as a promoter and/or operator. Other typical features may include appropriate ribosome binding sites, termination codons, enhancers, terminators, or replicon elements. These additional features can be inserted into the vector at the appropriate site or sites by conventional splicing techniques such as restriction endonuclease digestion and ligation.

Yeast expression systems, which are one variety of recombinant eukaryotic expression systems, generally employ *Saccharomyces cerevisiae* as the species of choice for expressing recombinant proteins. *S. cerevisiae* and similar yeasts possess well known promoters useful in the construction of yeast expression systems, including but not limited to GAP491, GAL10, ADH2, and alpha mating factor.

Yeast vectors useful for constructing recombinant yeast expression systems for expressing HCMV include, but are not limited to, shuttle vectors, cosmids, chimeric plasmids, and those having sequences derived from 2-micron circle plasmids.

Insertion of the appropriate DNA sequence coding for HCMV or stable mutant thereof, into these vectors will, in principle, result in a useful recombinant yeast expression system for HCMV where the modified vector is inserted into the appropriate host cell, by transformation or other means.

One preferred expression system is with baculovirus, under the control of the polyhedrin promoter. See, e.g., D. R. O'Reilly et al., *Baculovirus Expression Vectors: A Laboratory Manual* W. H. Freeman 1992, for a background description of this expression technology.

Recombinant mammalian expression systems are another means of producing the recombinant HCMV for the conjugates of this invention. In general, a host mammalian cell can be any cell that has been efficiently cloned in cell culture. Host mammalian cells useful for the purposes of constructing a recombinant mammalian expression system include, but are not limited to, Vero cells, NIH3T3, GH3, COS, murine C127 or mouse L cells. Mammalian expression vectors can be based on virus vectors, plasmid vectors which may have SV40, BPV or other viral replicons, or vectors without a replicon for animal cells. Detailed discussions on mammalian expression vectors can be found in the treatises of Glover, D. M. (ed.) "DNA Cloning: A Practical Approach," IRL 1985, Vols. I and II.

Recombinant HCMV may possess additional and desirable structural modifications not shared with the same organically synthesized peptide, such as adenylation, carboxylation, glycosylation, hydroxylation, methylation, phosphorylation or myristoylation. These added features may be chosen or preferred as the case may be, by the appropriate choice of recombinant expression system. On the other hand, recombinant HCMV may have its sequence extended by the principles and practice of organic synthesis.

Dependence of Protease Specific Activity on Enzyme and Glycerol Concentrations

Dilution of a concentrated solution of HCMV protease produces a time-dependent change in activity to a new, lower level. The rate and extent of the change in protease activity is a function of temperature. At 37° C., the decrease in protease activity occurs within minutes, while at 0° C., no significant change is observable for a period of hours. The change in HCMV protease activity at four temperatures upon dilution as a function of time shows that increases in temperature associate with more rapid decay of protease activity. At temperatures above 20° C., the change in activity ($t_{1/2} \leqq 30$ min) upon enzyme dilution is such that an accurate assessment of activity requires a rapid assay (ca. 1 min).

The specific activity of the HCMV protease increases at higher enzyme and glycerol concentrations. The specific activities of the protease measured after enzyme dilution and incubations of 1.5 hr and 3.5 hr prior to reaction reveal that the HCMV protease specific activity tends toward zero as its concentration is lowered. The negligible difference between the determinations at 1.5 and 3.5 hr suggests that the active form of the enzyme has reached equilibrium within 1.5 hr, for both the 10% and 20% glycerol samples. The activity of the protease incubated in 10% glycerol (v/v) is lower than that incubated in 20% glycerol (v/v). It can be shifted back to the higher activity seen for 20% glycerol by addition of an equal volume of buffer containing 30% glycerol to produce a solution containing 20% glycerol, followed by further incubation. Thus, the dependence of HCMV protease activity on enzyme and glycerol concentrations is reversible.

The dependence of HCMV protease activity on enzyme concentration can be interpreted in terms of a monomer-dimer equilibrium wherein only the dimeric form of the enzyme is active. Using this equilibrium expression, the dissociation constant ($K_d$) for dimer dissociation is 0.55 $\mu$M at 30° C. in 20% glycerol. The implication of this $K_d$ value is that the enzyme will be predominantly monomeric and inactive when assayed at low concentrations (less than 200 nM) with these solvent conditions. Hence, a low temperature such as 0° C. is needed to preserve the active, dimeric form of the enzyme.

Analytical Centrifugation

The quaternary state of the HCMV protease was characterized by sedimentation velocity measurements. Table 1 shows the results of sedimentation analyses of samples at a concentration of 20 mM in the presence or absence of 20% glycerol (v/v). An approximate solution of the Lamm equation fits directly to the data to obtain the sedimentation coefficient, $S_{20}$,w, the diffusion coefficient, $D_{20}$,w, and by use of the Svedberg relation, the molecular weight. For both samples good fits are found for a single sedimenting species. In the absence of glycerol the molecular weight obtained is 29.7 kDa which is close to the molecular weight of a monomeric HCMV protease. In 20% glycerol, 48.5 kDa is obtained, indicating that the enzyme is in a predominantly dimeric form. The increase in $S_{20},w$ and the decrease $D_{20},w$ shown in Table 1 are both consistent with the existence of a stable dimeric protease in 20% glycerol.

Size Exclusion Chromatography

The HCMV protease preincubated in the absence of glycerol and applied to a size exclusion column elutes with an apparent molecular weight of 37 kDa or 56 kDa depending on the loading concentration of the protease. With 20% glycerol present during preincubation, the protease elutes as a single 56 kDa species except with relatively low protease loading concentrations (<10 mM), where two fractions emerge with apparent weights of 55 kDa and 33 kDa. Since the molecular weight of the HCMV protease calculated from amino acid sequence is 28 kDa, these results suggest that the protease exists in a monomer-dimer equilibrium. Eluted enzyme samples corresponding to a dimeric protease show no evidence of covalent (disulfide) linkages as demonstrated by SDS-PAGE under non-reducing conditions. The elution profiles examined as a function of the enzyme sample concentration in 20% glycerol, at 30° C., are shown in FIG. 1.

Figure 2:
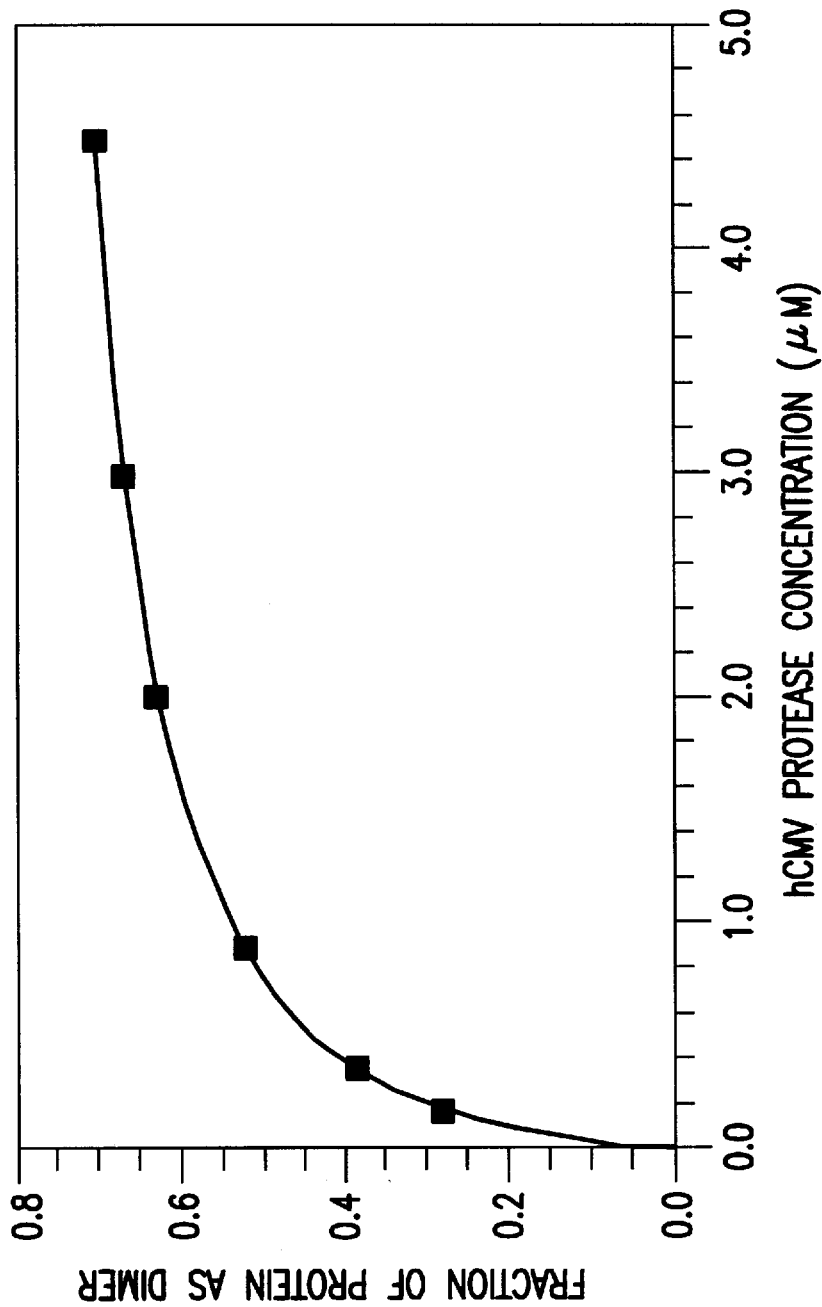
FIG. 2. Fraction of total protein appearing in the dimer peak (26.2 min) as a function of protein concentration. The solid line corresponds to a fit of the monomer-dimer equilibrium function to the data, yielding a $K_d$ of 0.54 mM, with a maximum dimer fraction of 0.92. Same conditions as in FIG. 1.

Assignment of the early (55 kDa) and late (33 kDa) elution peaks in FIG. 1 as dimer and monomer, respectively, allows the estimation of a $K_d$ for dimerization. Using the ratios of the areas under-the-peak of the early and late peaks, a $K_d$ value of 0.54 mM is found for 20% glycerol as shown in FIG. 2. The maximum fraction of dimeric protease extrapolated from FIG. 2 is 0.92. In separate experiments using protease at a loading concentration of 100 mM, the maximum fraction of dimeric protease is more than or equal to 0.95. When activity assays are conducted at 0° C., no detectable activity is found in the eluted peak corresponding to the monomer while hydrolytic activity (more than 50-fold of detectable levels) is found for the dimer peak. The same analysis applied to enzyme pre-equilibrated in 10% glycerol produces a

TABLE 1

Velocity sedimentation of HCMV protease[a]

| Glycerol (%, v/v) | $S_{20,w}$ | $D_{20,w}$ ($cm^2 \times 10^7$) S | Mol. Wt.- (kDa) |
|---|---|---|---|
| 0 | 2.78 S [2.77, 2.79] | 8.34 [8.25, 8.45] | 29.7 [29.2, 30.1] |
| 20 | 3.59 S [3.58, 3.60] | 6.57 [6.45, 6.67] | 48.5 [47.6, 49.6] |

[a]Samples were loaded at 20 mM (monomer equivalents) and sedimentation was conducted at 20° C. Data shown in brackets are the 95% confidence limits.

$K_d$ of 5.5 mM. Calculations give average dissociation constants ($K_d$) for HCMV protease of 6.6 mM in 10% glycerol and 0.55 mM in 20% glycerol.

Changes in sample loading volume, column temperature, and chromatography time have been studied to confirm that equilibrium exchange between protease monomers and dimers is negligible during size exclusion chromatography. No significant variation in dimer-monomer peak ratios occurs when injection volumes of 5, 10, 20, or 30 ml (15–90 pmol) of protease sample are made. Column temperatures of 5°, 10°, and 18° C. produce essentially identical results as well. Some coalescence of elution peaks toward the monomeric form is observed at 25° C., and complete peak merging occurs at 30° C. to yield mostly monomer. With the chromatography temperature at 10° C., as in the analyses presented here, the dimer-monomer ratio has also been compared for the use of one versus two sizing columns. While the resolution with two columns in tandem is slightly better than with one column alone, the dimer-monomer ratio observed is identical, although the chromatography runs are completed in one half the time with the single column. Despite an approximate 100-fold dilution of sample during the chromatography at 10° C., the aggregation state of the sample upon injection is well approximated by the elution patterns observed, due to the slow monomer-dimer equilibrium at low temperatures.

LOW TEMPERATURE PROTEASE ASSAY

Applicants have discovered that a low temperature promotes the formation of dimerization of the HCMV protease, providing a highly sensitive assay for screening inhibitors of the protease.

The low temperature assay may be conducted at a temperature between about 10° C. and about −10° C. A preferable range is between about +2° C. and about −2° C., most preferably at about 0° C.

The source of the HCMV protease is not a critical factor to the assay. Applicants use a convenient recombinant wild-type HCMV protease, as well as recombinant mutant forms, e.g., V141G/V207G which promotes stability through lowered autocatalysis. Other suitable sources include HCMV protease expressed in other recombinant systems, including mammalian and procaryotic expression systems. Natural enzyme purified from large lots of HCMV-infected cell lines are another suitable source, as well as synthetic enzymes.

A wide variety of substrates for HCMV protease are suitable for the low temperature assay of the present invention. The substrate needs tagging, e.g., with fluorescent or radioactive markers. Convenient substrates used in the experiments outlined herein are commercially produced, and include (Dabcyl)—RGVVNASSRLA—(Edans), (SEQ. ID. NO.: 4) (commercial product of Bachem Bioscience, Philadelphia, Pa.), and Ac-RWGVVN.Abu. RLATR—amide (SEQ. ID. NO:. 5 & SEQ. ID. NO: 6) (commercial product of Midwest Biotech, Indianapolis, Ind.) (Abu is amino-butyrate).

A wide variety of standard buffers are suitable for the low temperature assay of this invention. Typically, a buffer with low concentrations of a protein to reduce non-specific interactions and sticking, e.g., 0.05% BSA. Another preferred component commonly added to the buffer is glycerol, in concentrations of about 5% to about 30%, preferably about 10% to about 20%.

Applicants have discovered that increasing the substrate concentration increases dimerization. Substrate concentration may vary from about 0.0005 mg/ml to about 0.1 mg/ml. One preferred concentration is 0.04 mg/ml.

Applicants have also discovered that low enzyme concentration increases the sensitivity of the low temperature assay. Final HCMV protease concentrations are between about 1 nM to about 150 nM, preferably at about 15 nM.

EXAMPLE 1

Cloning and Expression of the HCMV Protease

HCMV strain AD169 DNA was prepared from supernate virions as previously described [LaFemina, R. L., et al., J. Gen Vir., 64, 373 (1983)]. The N-terminal 256 amino acid protease domain was PCR amplified using primers derived from the DNA sequence as described by Chee, M. S., et al., Curr. Top Microbiol. Immunol., 154, 125 (1990), Genbank accession number X17403. The sequence of the N-terminal primer was 5'GCTAGGCTCATATGACGATGGACGAG- CAGCAG (SEQ ID NO: 1), while the sequence of the C-terminal primer was 5'GCTAGGCTAGATCTTTACGC-CTTGACGTATGACTCGC (SEQ ID NO: 2). PCR conditions consisted of: 6 cycles with 0.5 min denaturation at 97° C., 1.5 min annealing at 60° C. and 2 min extension at 72° C., 25 cycles with 1 min denaturation at 94° C. and annealing and extension as above; followed by 6 cycles with 1 min denaturation at 94° C., 1.5 min annealing at 60° C. and 4 min extension at 72° C. The amplified DNA was digested with NdeI and BglII prior to ligation into the NdeI and BamHI sites of the T7 expression vector pET3c. The resulting plasmid, pT7CMVPr-4, was introduced into *E. coli* BL21DE3 for expression. Expression was induced by standard IPTG induction for 2 hr.

EXAMPLE 2
Protease Enzyme Purification

All purification steps were performed at 0° to 4° C. For the mutant form, with V141G and V207G mutations (V141G and V207G each render CMV protease resistant to autoproteolysis, see e.g. Sardana, V., et al., J. Biol. Chem, 269, 14339 (1994)), lysis of cells was performed with a microfluidizer in 50 mM TrisHCl, pH 8.0 buffer containing 10% glycerol, 25 mM NaCl, 1 mM EDTA, 1 mM DTT and 1 mM 4-(2-aminoethyl)-benzenesulfonylfluoride. The lysate was centrifuged and the pellet was washed with lysis buffer plus 0.1% NP40 and recentrifuged. Inclusion bodies were dissolved with 7M urea, 50 mM Tris HCl, 5 mM DTT, pH 8.0, followed by centrifugation and chromatography on an anion exchange column. Elution was performed using a sodium chloride gradient in the urea-containing buffer. Protein folding was accomplished by dilution of protease-containing fractions to 0.2 mg/ml into 25 mM Tris HCl (pH 7.5), 10% glycerol, 5 mM DTT, and i M guanidine HCl followed by dialysis in the same buffer without guanidine HCl for 24 hr. The resulting protein solution was chromatographed on an anion exchange column and eluted with a sodium chloride gradient in 25 mM TrisHCl (pH 7.5), 10% glycerol, 1 mM EDTA, and 1 mM DTT to yield the purified enzyme.

The wild-type HCMV protease was purified similarly. To avoid self-proteolysis, the protein obtained from the first anion exchange step was folded and dialyzed as above, but in the absence of glycerol. The sample was then acidified to pH 5.5 with MES, applied to a cation exchange column in 50 mM MES, 1 mM EDTA, 1 mM DTT, pH 5.5, and eluted with a sodium chloride gradient. The wild-type enzyme was stable at pH 5.5 and returned to full activity following dilution to pH 7.5. Enzyme preparations were greater than 95% pure by SDS PAGE and gave the expected amino acid analysis. The N-terminal 5 residues of both enzymes were MTMDE, showing retention but defonnylation of the initial N-formyl methionine. Electrospray mass spectrometry indicated a single species within 10 a.m.u. of the expected mass. The concentrations of stock enzyme solutions were determined by quantitative amino acid analysis.

EXAMPLE 3
Substrate Cleavage Assay, Monomer

Peptide substrates were organically synthesized with a peptide synthesizer and were >95% pure. The peptide cleavage assay was performed at room temperature in 50 $\mu$l of 100.0 mM Hepes buffer (pH 7.5), 5.0 mM DTT, 1.0 mM EDTA, 25.0 mM NaCl, 0.05% bovine serum albumin. After 20 mins, the reaction was quenched by addition of 50 $\mu$l 10% phosphoric acid and the mixture was analyzed by reverse phase HPLC on a 3.9×75 mm column. The cleavage products were resolved using a 0.1% phosphoric acid/acetonitrile gradient and identified by either N-terminus sequence analysis or retention time comparison with authentic peptide. Absorbance of the eluate was monitored at 210 nm using a photodiode array detector. The enzyme concentration used in the assay varied from 150 to 1500 nM depending on the substrate used. Each substrate peptide was titrated from 50 $\mu$M to 5.0 mM. Kinetic parameters ($k_{cat}$ and km) were determined by fitting the velocity (initial rates at <5.0% of total substrate hydrolysis) versus substrate concentration data to the Michaelis-Menton equation (hyperbolic). The initial velocity and steady-state conditions for the enzyme reaction were established for each peptide substrate.

EXAMPLE 4
Assay for HCMV Protease Inhibition Mutant Enzyme Form, Monomer

The recombinant human cytomegalovirus protease (with V141G and V207G substitutions, 256 amino acids, 20 nM) cleaves the peptide substrate $^3$H-Acetyl Gly Val Val Asn Ala Ser Cys Arg Leu Arg Arg amide (1 mM) (SEQ ID NO: 3) at the Ala Ser bond. The assay is performed in 100 mM Hepes (pH 7.5), 1 mM EDTA 0.05% BSA, 25 mM NaCl (50 ml total volume) and quenched by adding 50 ml of 5% phosphoric acid. The assay mix is transferred to a tube containing Dowex ion exchange, the tubes are rinsed with water (2×200 ml). The cleaved radioactive peptide in the supernatant is quantitated by a scintillation counter. Reduction in radioactivity in presence of compounds gives the measure of inhibition, and is determined as the concentration of inhibitory compound giving 50% inhibition or $IC_{50}$.

EXAMPLE 5
Low Temperature Assay for Human Cytomegalovirus Protease in Dimeric Form The following protocol is suitable for either the V141G/V207G mutant protease enzyme or the wild-type enzyme.

Purified HCMV protease (256 amino acids, mature form) was reacted with the fluorogenic HCMV protease peptide substrate fluorophore-labeled (Dabcyl)—RGVVNASSRLA—(Edans), (SEQ ID NO: 4) (commercial product of Bachem Bioscience, Philadelphia, Pa.), according to the following protocol.
Final Buffer Concentrations
100 mM Hepes pH 7.5
5 mM DTT (Dithiothreitol)
1 mM EDTA
0.05% BSA
20% Glycerol
Substrate concentration=0.04 mg/ml
Assay volume=100 ul
Final CMV Protease concentration=15.0 nM
Time of assay=90 min
Assay Temperature=0° C.
Assay Quench Solution
4M Urea in water—100 ul per reaction
Procedure Buffer components are mixed together on the day of the assay from stock solutions. BSA and DTT stocks are stored frozen at −20° C. The substrate stock solutions are 1.0 mg/ml substrate reconstituted in water, stored frozen until needed. Enzyme stock solutions (0.5–12mg/ml) are stored frozen at −70° C. Enzyme dilutions are made in the complete reaction buffer minus substrate.

Combine, in a low fluorescent microtiter plate a 5 ul aliquot of sample comtaining DMSO with 55 ul reaction buffer containing the substrate. Take a fluorescence reading of this mixture for a pre-enzyme baseline. At this point reactions are incubated at 0° C. Initiate reaction with 40 ul of CMV Protease in reaction buffer. Incubate reactions (at 0°

C.) for 90 minutes, quench reaction with 100 ul 4M Urea and take fluorescence reading, determine % inhibition for each compound tested. Confirm on HPLC.

While the foregoing specification teaches the principles of the present invention, with examples provided for the purpose of illustration, it will be understood that the practice of the invention encompasses all of the usual variations, adaptations, modifications, deletions or additions of procedures and protocols described herein, as come within the scope of the following claims and its equivalents.

What is claimed is:

1. A low temperature assay for the detection of compounds that inhibit human cytomegalovirus protease, said assay having a procedure comprising the steps of:
   a) providing a quantity of a compound or compounds to be assayed for inhibitory activity;
   b) incubating said compound or compounds with human cytomegalovirus protease at a temperature between about 10° C. and about −10° C. in a peptide substrate cleavage assay; and
   c) determining the inhibition of said protease by comparing the reduction in radioactivity of the cleaved peptide in the presence of said compound or compounds against the radioactivity of the cleaved peptide without said compound or compounds, said reduction in radioactivity being determined as the concentration of compound or compounds giving about 50% inhibition.

2. The assay of claim 1, wherein the incubation of step (b) is carried out at a temperature range of between about 2° C. and about −2° C.

3. The assay of claim 1, wherein the incubation of step (b) is carried out at a temperature of about 0° C.

* * * * *